United States Patent
Grigsby, Jr. et al.

(10) Patent No.: US 7,351,859 B2
(45) Date of Patent: Apr. 1, 2008

(54) HEAT ACTIVATED TERTIARY AMINE URETHANE CATALYSTS

(75) Inventors: Robert A. Grigsby, Jr., Austin, TX (US); Robert L. Zimmerman, Austin, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 471 days.

(21) Appl. No.: 10/838,136

(22) Filed: May 3, 2004

(65) Prior Publication Data

US 2005/0027002 A1 Feb. 3, 2005

Related U.S. Application Data

(60) Provisional application No. 60/466,990, filed on May 1, 2003.

(51) Int. Cl.
*C07C 55/06* (2006.01)
(52) U.S. Cl. .................................................... 562/597
(58) Field of Classification Search ..................... None
See application file for complete search history.

(56) References Cited

U.S. PATENT DOCUMENTS

| 2,932,621 | A | * | 4/1960 | Terry ........................... 521/118 |
| 3,980,594 | A | | 9/1976 | Fabris et al. ........... 260/2.5 AC |
| 4,521,545 | A | | 6/1985 | Kerimis et al. .............. 521/107 |
| 4,608,407 | A | | 8/1986 | Kerimis et al. ................ 524/14 |
| 4,617,286 | A | * | 10/1986 | Arai et al. ................... 502/167 |
| 6,007,649 | A | | 12/1999 | Haas et al. ................. 156/62.2 |

OTHER PUBLICATIONS

PCT/US04/13770, International Search Report; Dated Jan. 13, 2005.
PCT/US/04/13770; Supplemental International Search Report; Dated May 6, 2005.

* cited by examiner

*Primary Examiner*—Paul A. Zucker
(74) *Attorney, Agent, or Firm*—O'Keefe, Egan & Peterman LLP

(57) ABSTRACT

This invention concerns a compound formed from a tertiary amine-carboxylic acid salt, where the carboxylic acid and tertiary amine are selected such that the catalyst salt is blocked at room temperature and becomes unblocked at an elevated temperature. The compound is useful as a heat activated urethane catalyst.

10 Claims, 6 Drawing Sheets

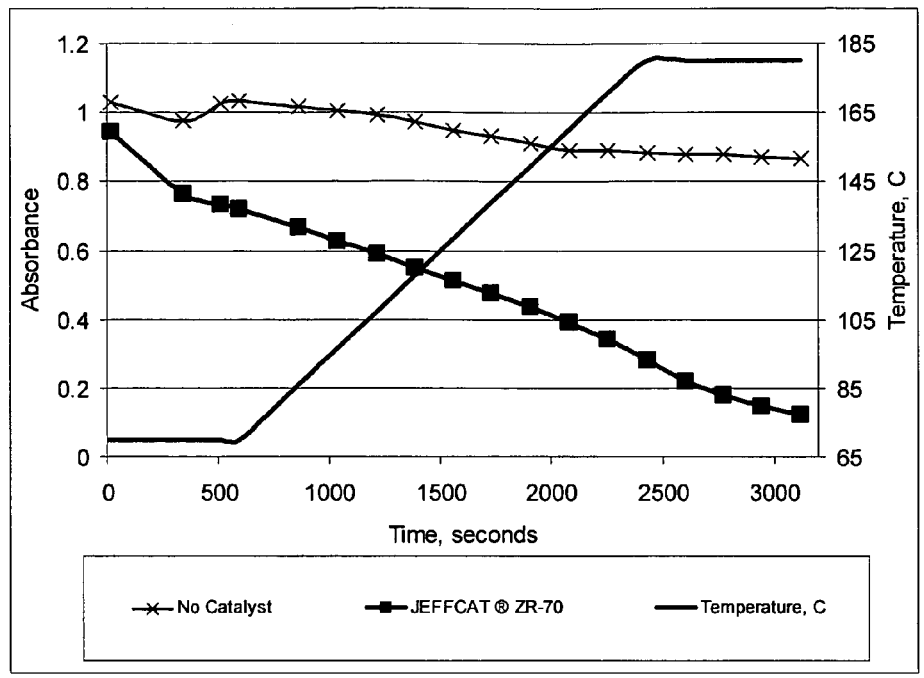
FIG. 1 - Isocyanate Absorbance, 2290 cm$^{-1}$
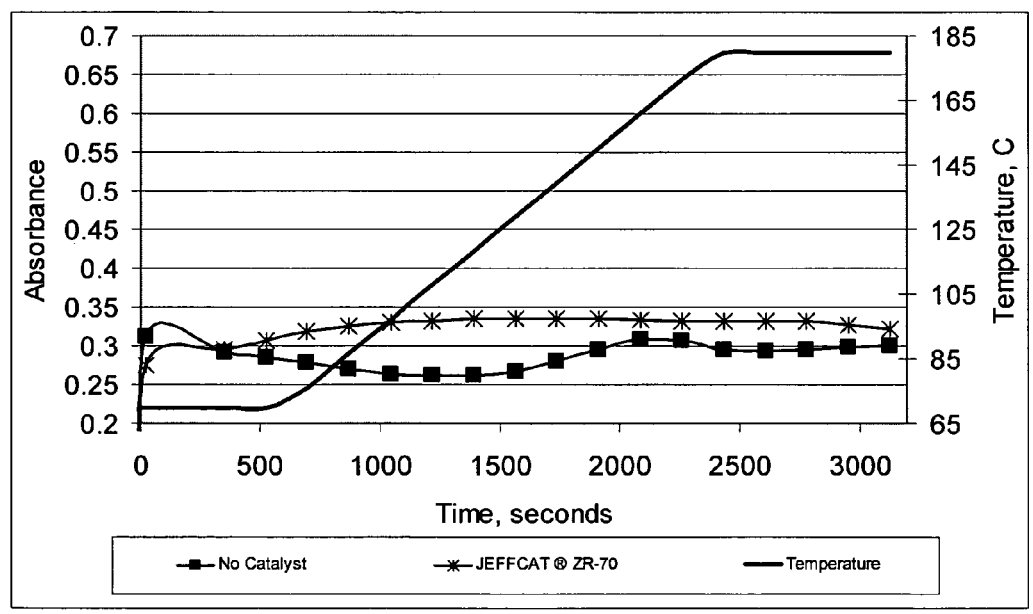
FIG. 2 - Carbonyl Absorbance, 1730-1680 cm$^{-1}$

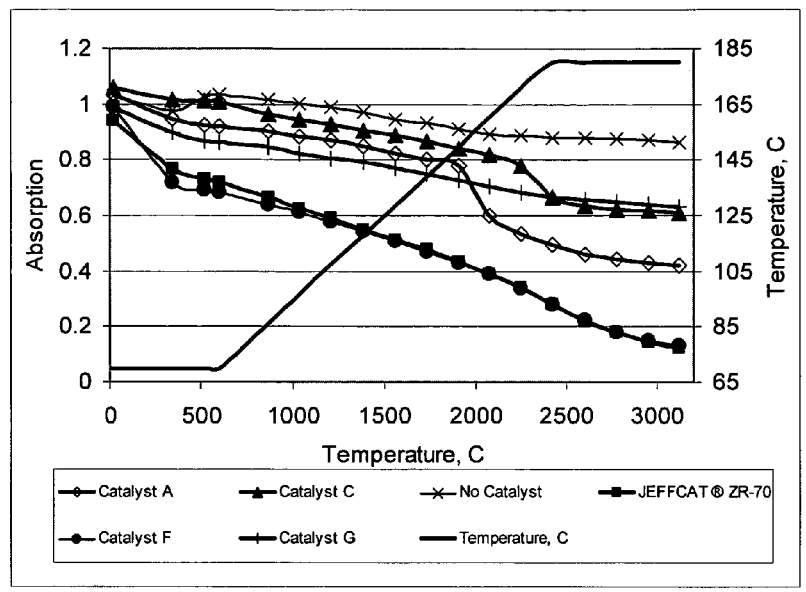
FIG. 3 - Isocyanate Absorbance, 2290 cm$^{-1}$
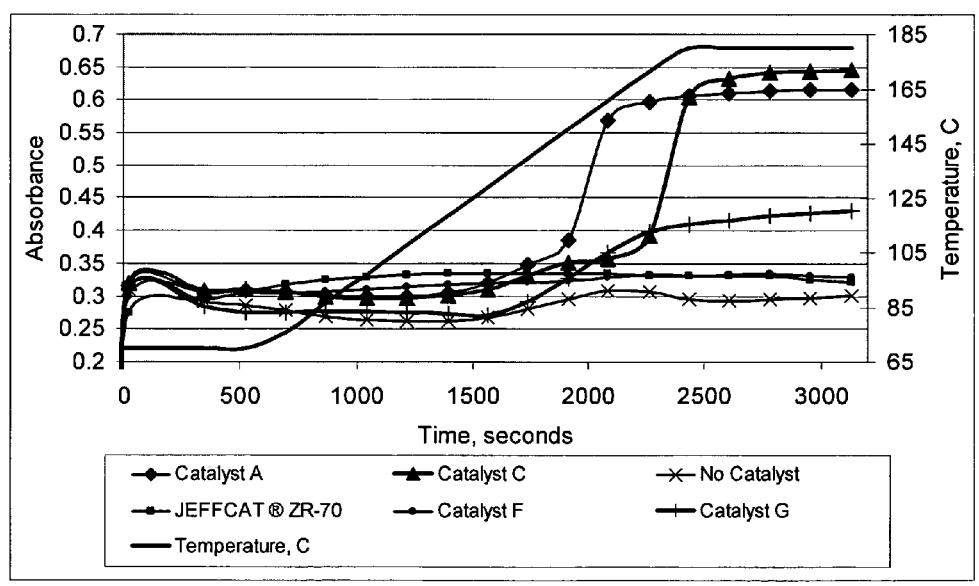
FIG. 4 - Carbonyl Absorbance, 1730-1680 cm$^{-1}$

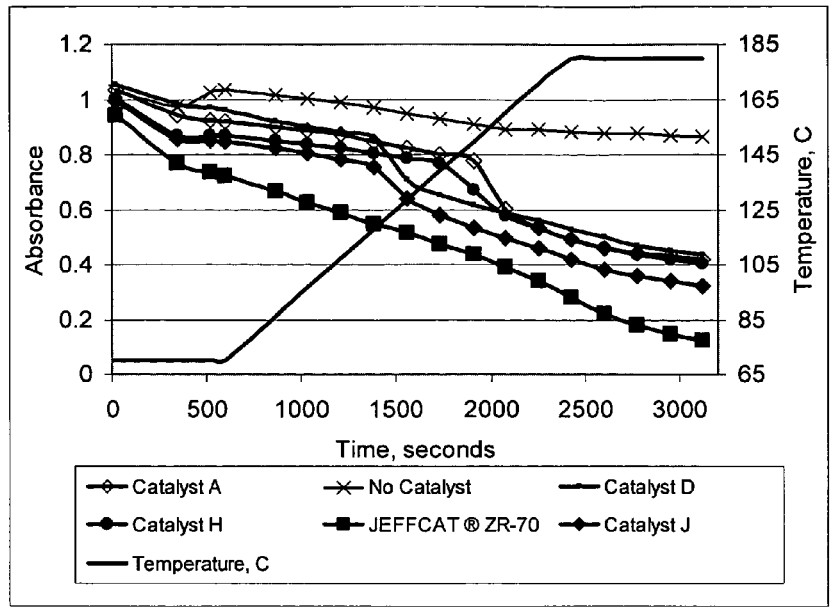
FIG. 5 - Isocyanate Absorbance, 2290 cm$^{-1}$
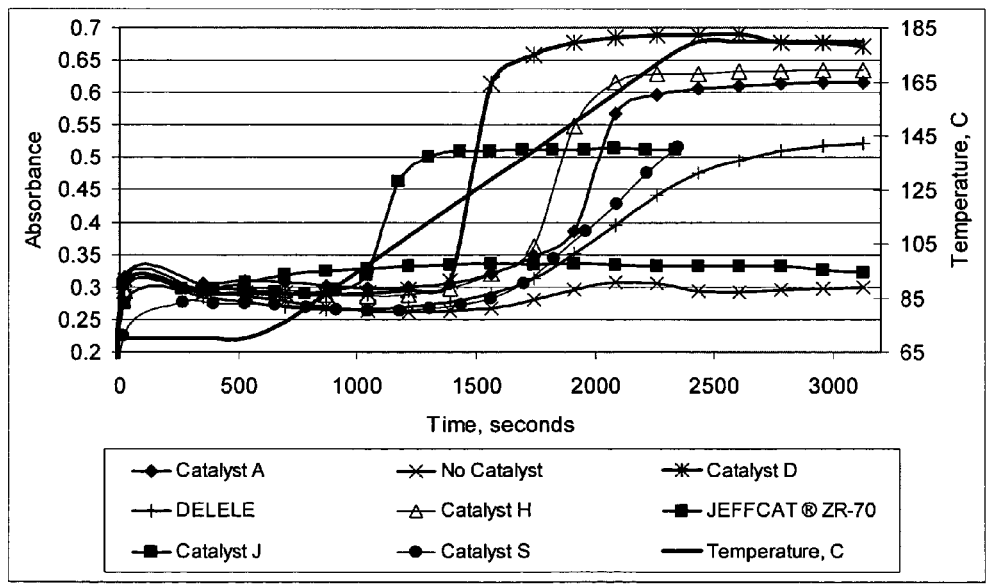
FIG. 6 - Carbonyl Absorbance, 1730-1680 cm$^{-1}$

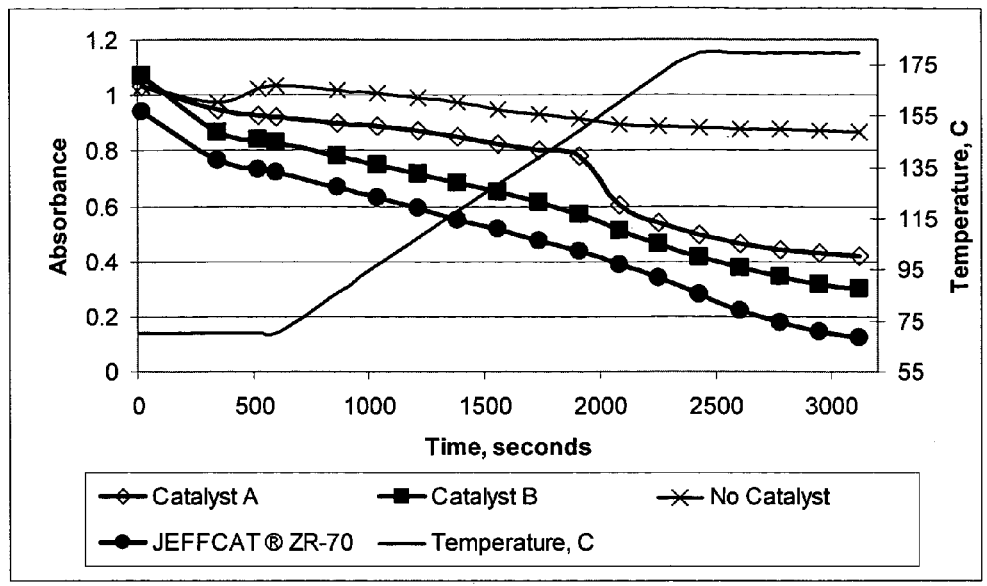
FIG. 7 - Isocyanate Absorbance, 2290 cm$^{-1}$
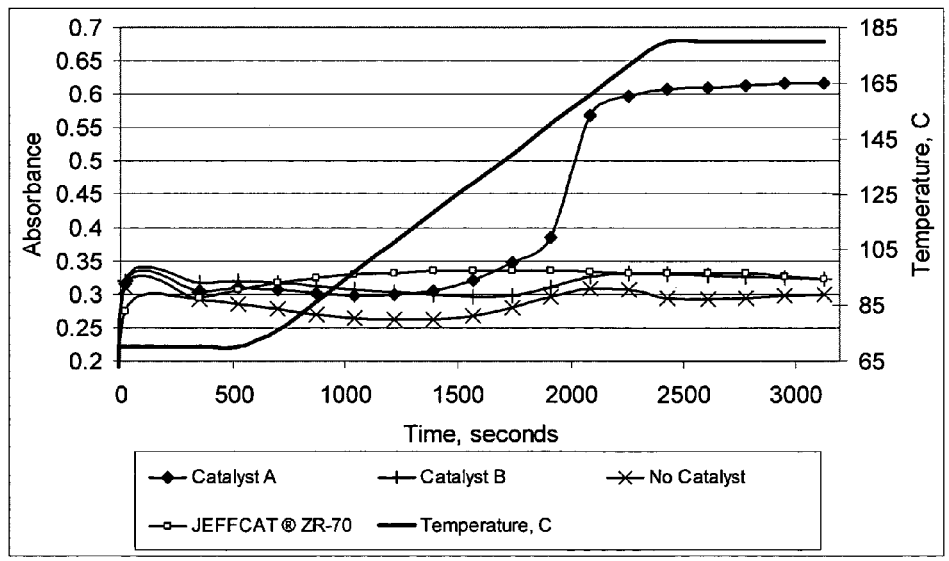
FIG. 8 - Carbonyl Absorbance, 1730-1680 cm$^{-11}$

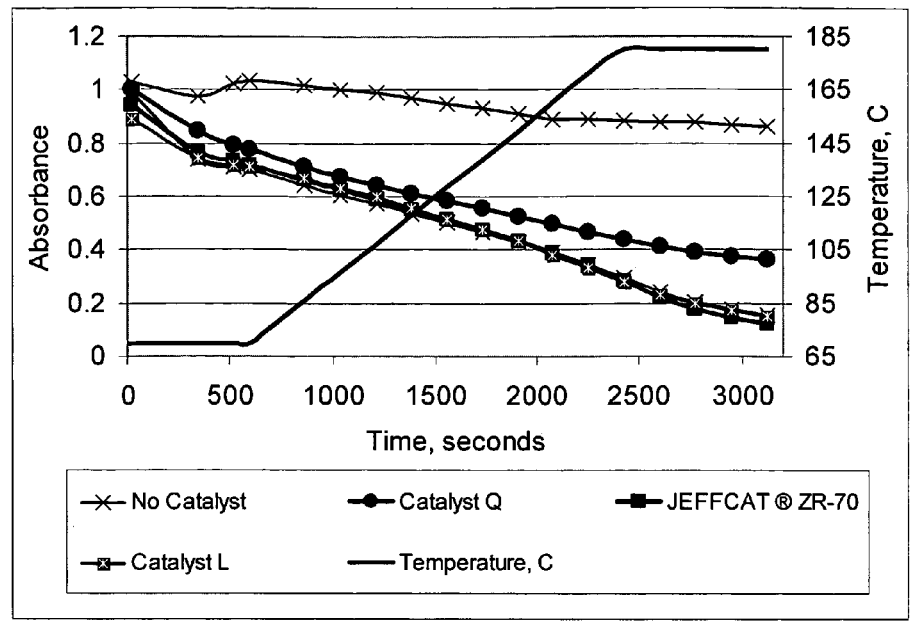
FIG. 9 - Isocyanate Absorbance, 2290 cm$^{-1}$
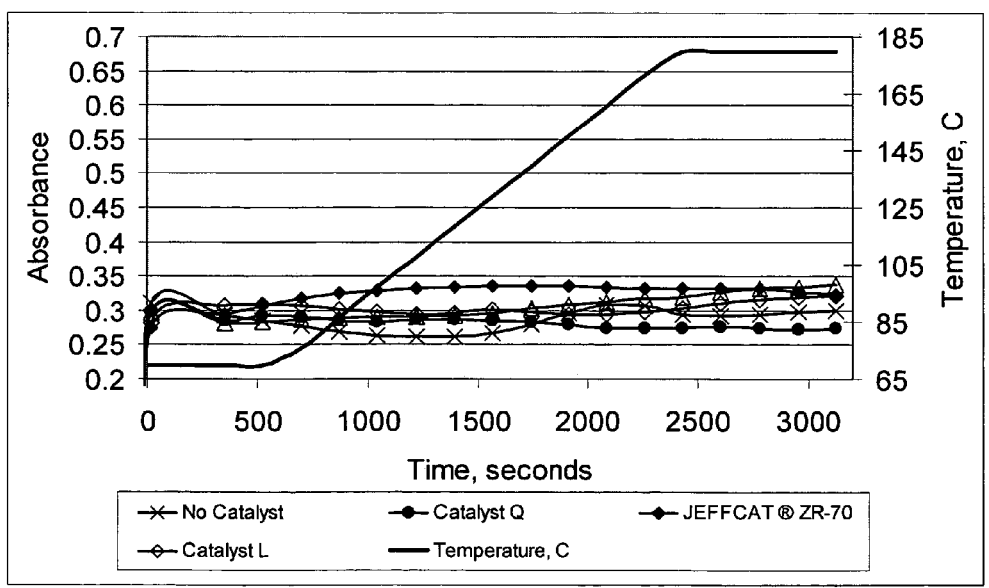
FIG. 10 - Carbonyl Absorbance, 1730-1680 cm$^{-1}$

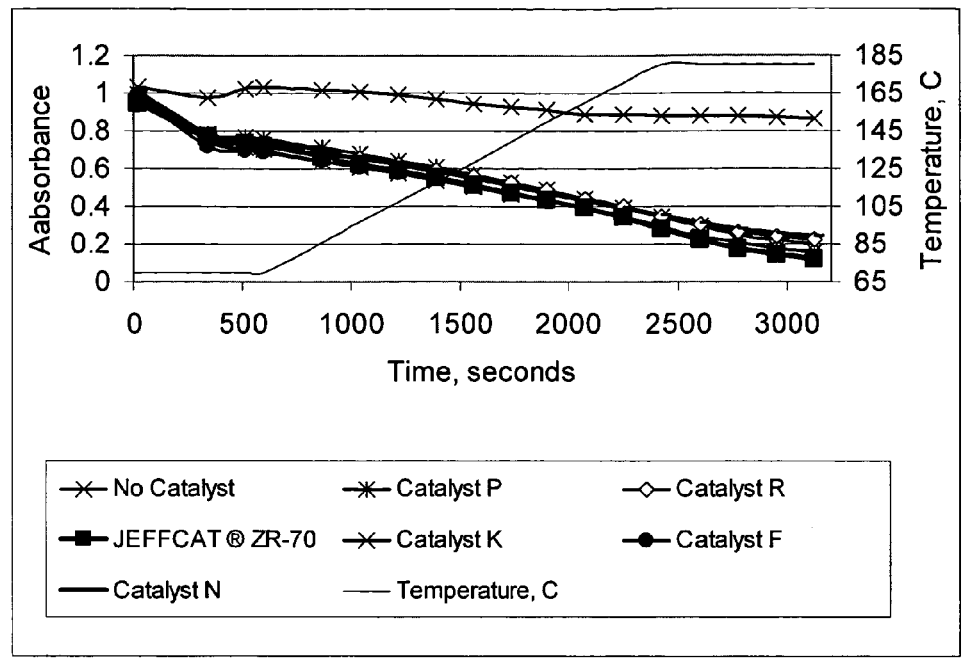
FIG. 11 - Isocyanate Absorbance, 2290 cm$^{-1}$
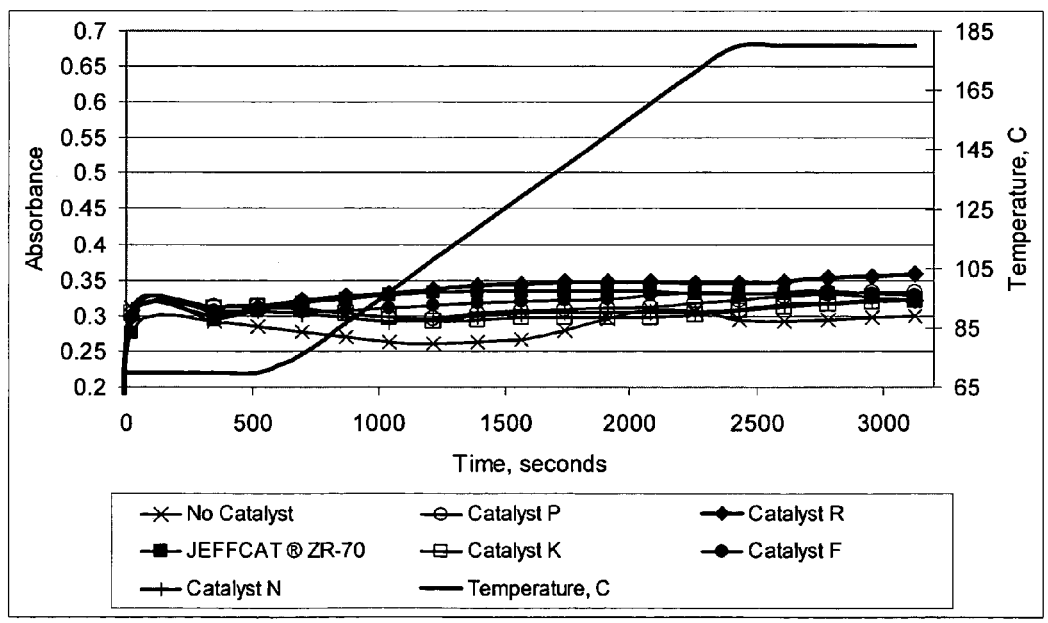
FIG. 12 - Carbonyl Absorbance, 1730-1680 cm$^{-11}$

HEAT ACTIVATED TERTIARY AMINE URETHANE CATALYSTS

This application claims priority to U.S. provisional patent application Ser. No. 60/466,990, filed May 1, 2003.

BACKGROUND OF INVENTION

This invention pertains to compounds useful as a heat activated urethane catalyst that are formed from a tertiary amine-carboxylic acid salt, where the carboxylic acid and tertiary amine are selected such that the compound unblocks at a given temperature.

Urethane is frequently polymerized through use of a catalyst such as a tertiary amine. The inventors herein have recognized that a need exists for a catalyst that is essentially inert at normal temperatures during storage, and which becomes active at an elevated temperature.

SUMMARY OF INVENTION

The present invention provides a solution to one or more of the disadvantages and deficiencies described above.

In one broad respect, this invention is a heat activated urethane catalyst which comprises a tertiary amine-carboxylic acid salt. This salt is blocked and inactive at room temperature, but becomes unblocked at an elevated temperature (it is heat activated). By unblocked it is meant that the tertiary amine becomes a free, neutral compound and is not present as a salt of the carboxylic acid. By elevated temperature it is meant, for example, a temperature above about 110° C., or above about 125° C., or above about 135° C., or higher. In general, the salt becomes unblocked at a temperature above 135° C. In the acid salt, the tertiary amine may be N,N-dimethylcyclohexylamine, pentamethyldiethlenetriamine, N,N-dimethyl-2(2-aminoethyoxy)ethanol, pentamehyldipropylenetriamine, tetramethyldipropylenetriamine, dimethylaminoethoxyethanol, N,N,N'-trimethylaminoethyl-ethanolamine, 2-(dimethylamino)-ethanol, or a combination thereof; the tertiary amine may be dimethylaminoethoxy-ethanol, N,N,N'-trimethylaminoethyl-ethanolamine, 2-(dimethylamino)-ethanol, or a combination thereof; the carboxylic acid may contain less than 30 carbons; the carboxylic acid may be oxalic acid, salicylic acid, or a combination thereof; the amine may be N,N-dimethyl-2-(2-aminoethyoxy) ethanol, the carboxylic acid is oxalic acid, and are present in a mole ratio of about 1:1; the mole ratio of tertiary amine to carboxylic acid may be less than 2:1; the mole ratio of tertiary amine to carboxylic acid may be less than about 1.5; the mole ratio of tertiary amine to carboxylic acid may be from about 0.9:1 to about 1.1; the acid salt may produce a carbonyl absorbance of at 1730-1680 cm$^{-1}$ of at least 0.5 above 135° C.; or any combination thereof.

In another broad respect, this invention is a process for the manufacture of a tertiary amine-carboxylic acid salt that becomes unblocked above about 110° C., or above about 125° C., or above about 135° C., or higher, comprising: reacting a tertiary amine with a carboxylic acid to form the tertiary amine-carboxylic acid salts. In this process effective types and amounts of carboxylic acid and a tertiary amine are reacted to form a tertiary amine:carboxylic acid salt, wherein the carboxylic acid and tertiary amine are selected such that the salt for example unblocks at a temperature above about 110° C., or above about 125° C., or above about 135° C., or higher. Thus the carboxylic acid and tertiary amine are selected, and provided in amounts, such that the resulting salt unblocks at a temperature above about 110° C., or above about 125° C., or above about 135° C., or a given higher temperature. In this process, the tertiary amine may be N,N-dimethylcyclohexylamine, pentamethyldiethlenetriamine, N,N-dimethyl-2(2-aminoethyoxy)ethanol, pentamehyldipropylenetriamine, tetramethyldipropylenetriamine, dimethylaminoethoxyethanol, N,N,N'-trimethylaminoethyl-ethanolamine, 2-(dimethylamino)-ethanol, or a combination thereof; the tertiary amine may be dimethylaminoethoxy-ethanol, N,N,N'-trimethylaminoethyl-ethanolamine, 2-(dimethylamino)-ethanol, or a combination thereof; the carboxylic acid may contain less than 30 carbons; the carboxylic acid may be oxalic acid, salicylic acid, or a combination thereof; the amine may be N,N-dimethyl-2-(2-aminoethyoxy) ethanol, the carboxylic acid is oxalic acid, and are present in a mole ratio of about 1:1; the mole ratio of tertiary amine to carboxylic acid may be less than 2:1; the mole ratio of tertiary amine to carboxylic acid may be less than about 1.5; the mole ratio of tertiary amine to carboxylic acid may be from about 0.9:1 to about 1.1; the acid salt may produce a carbonyl absorbance of at 1730-1680 cm$^{-1}$ of at least 0.5 above 135° C.; or any combination thereof.

In another broad respect, this invention is a process for the manufacture of polyurethane, comprising: combining a diisocyanate, a polyol, and a catalyst, wherein the catalyst is a tertiary amine-carboxylic acid salt that becomes unblocked above 135° C., and heating the resulting composition to unblock the salt to thereby polymerize the composition to form a polyurethane composition.

The catalyst of this invention can be used in the manufacture of a press molded material, such as by applying (for example, by spraying) diisocyanate, polyol, and a catalyst on wood material, wherein the catalyst is a tertiary amine-carboxylic acid salt that is blocked at room temperature and becomes unblocked at an elevated temperature, and heating (for example while under pressure so as to form a press molded material) the resulting mixture to a temperature effective to unblock the salt to produce unblocked tertiary amine.

The catalyst of this invention can be used for the production of orientated strand boards such as by applying a urethane composition on wood chips, applying such as by spraying a tertiary amine:carboxylic acid salt catalyst on the wood chips, compressing the chips, heating the compressed chips so that at least a portion of the salt catalyst unblocks to thereby initiate polymerization of the urethane composition. The urethane and salt may be sprayed separately or simultaneous in admixture.

The catalyst of this invention can be used to make a composite formed of wood chips and the polymerization product of a urethane composition and tertiary amine: carboxylic acid salt that unblocks at a temperature of at least 135° C.

In the practice of this invention, the tertiary amine may be N,N-dimethylcyclohexylamine, pentamethyldiethlenetriamine, N,N-dimethyl-2(2-aminoethyoxy)ethanol, pentamehyldipropylenetriamine, tetramethyldipropylenetriamine, dimethylaminoethoxyethanol, N,N,N'-trimethylaminoethyl-ethanolamine, 2-(dimethylamino)-ethanol, or a combination thereof; the tertiary amine may be dimethylaminoethoxy-ethanol, N,N,N'-trimethylaminoethyl-ethanolamine, 2-(dimethylamino)-ethanol, or a combination thereof; the carboxylic acid may contain less than 30 carbons; the carboxylic acid may be oxalic acid, salicylic acid, or a combination thereof; the amine may be N,N-dimethyl-2-(2-aminoethyoxy) ethanol, the carboxylic acid is oxalic acid, and are present in a mole ratio of about 1:1; the mole ratio of tertiary amine to carboxylic acid may be less than 2:1; the mole ratio of tertiary amine to carboxylic acid may be less than about 1.5; the mole ratio of tertiary amine to carboxylic acid may be from about 0.9:1 to about 1.1; the acid salt may produce for example a carbonyl absorbance of at 1730-1680 cm$^{-1}$ of at least 0.5 above 135° C.; the diisocyanate may be an aliphatic, cycloaliphatic, aromatic, heterocyclic diisocyanate, or combination thereof; the diisocyanate may be naphthalene bis (4-phenyl isocyanate), 4,4'-diphenylmethane diisocyanate, 1,3- and 1,4-phenylene diisocyanate, toluene 2,4- and 2,6-diisocyanate, diphenylmethane 2,4'- or 4,4'-diisocyanate, mixtures thereof or oligomers thereof or mixtures of oligomers the polyol may have two to eight hydroxyl groups; the diisocyanate and polyol may be employed so as to provide a NCO/OH ratio of from 1.1:1 to 10:1; or any combination thereof.

This invention has a number of advantages. For example, the tertiary amine-carboxylic acid salt of this invention is blocked and stable at room temperature and becomes unblocked. Advantageously, the unblocking occurs generally at a temperature above about 110° C., or above about 125° C., or above about 135° C., or at higher given temperatures.

In general, unblocking can be observed using Fourier transform infrared (FTIR) spectroscopy. Unblocking is generally indicated by a carbonyl absorbance at 1730-1680 cm$^{-1}$ of at least 0.5 above 135° C., and in another embodiment at least 0.5 above 150° C. The catalyst becomes active when it is unblocked, whereby polymerization of the urethane precursors commences.

Surprisingly, the catalyst of this invention shows little or no activity at room temperature but becomes active at elevated temperature. The activation temperature can be controlled by choice of the amine and carboxylic acid. An additional surprising result is the 1:1 mole ratio of N,N-dimethyl-2-(2-aminoethoxy)ethanol:oxalic acid gave this property while the 2:1 mole ratio of these components did not. N,N-dimethyl-2-(2-aminoethoxy)ethanol is available commercially under the name JEFFCAT ZR-70. In one embodiment, the mole ratio of tertiary amine to carboxylic acid is less than 2:1, in another embodiment is less than about 1.5, and in another embodiment is less than about 1.1. In one embodiment, the mole ratio of tertiary amine to carboxylic acid is from about 0.9:1 to about 1.1, and in another embodiment is about 1:1.

BRIEF DESCRIPTION OF THE DRAWINGS

FIG. 1 shows the difference in isocyanate absorbances between a catalyzed, unblocked system and a non-catalyzed system as per example 2.

FIG. 2 shows the difference in carbonyl absorbances between a catalyzed, unblocked system and a non-catalyzed system as per example 2.

FIG. 3 shows the differences in isocyanate absorbances for catalysts A, C, F, G, no catalyst, and JEFFCAT™ ZR-70 as per example 2.

FIG. 4 shows the difference in carbonyl absorbances for catalysts A, C, F, G, no catalyst, and JEFFCAT™ ZR-70 as per example 2.

FIG. 5 shows the isocyanate absorbances for catalysts A, D, H, J, S, no catalyst, and JEFFCAT™ ZR-70 as described in the examples.

FIG. 6 shows the carbonyl absorbances for catalysts A, D, H, J, S, no catalyst, and JEFFCAT™ ZR-70 as described in the examples.

FIG. 7 shows the difference in isocyanate absorbances for catalysts prepared from 1:1 mole ratio versus a mole ratio of 2:1 of tertiary amine to carboxylic acid.

FIG. 8 shows the difference in carbonyl absorbances for catalysts prepared from 1:1 mole ratio versus a mole ratio of 2:1 of tertiary amine to carboxylic acid.

FIGS. 9 and 11 show the isocyanate absorbances for certain catalysts which did not unblock.

FIGS. 10 and 12 show the carbonyl absorbances for certain catalysts which did not unblock.

DETAILED DESCRIPTION OF THE INVENTION

The tertiary amine—carboxylic acid salts of this invention can be prepared from a variety of starting compounds. The salts are made by contacting a tertiary amine with a carboxylic acid, typically in an aqueous mixture. The salts may be isolated and purified using standard techniques well known to one of skill in the art. The salts are used as heat activated catalysts for urethanes.

In general, the application of this technology in polyurethane involves heating a mixture of an isocyanate and some form of a hydroxyl type material in the presence of the blocked tertiary amine-carboxylic acid salt to a temperature such that the salt becomes unblocked, with the catalyst thereby becoming activated. The temperature at which the catalyst becomes unblocked may vary depending on the specific amine/acid salt at issue.

The tertiary amines used in the practice of this invention are selected such that the tertiary amine selected in combination with a given carboxylic acid is blocked at room temperature and becomes unblocked at elevated temperature, such as above about 110° C. and in one embodiment above about 125° C., and in another embodiment above about 135° C. In one embodiment, the catalyst may provide a carbonyl absorbance at 1730-1680 cm$^{-1}$ of at least 0.5 above 135° C. as measured in admixture with polyurethane precursors such as described. These tertiary amines may be referred to as effective tertiary amines, in the context of this invention. Tertiary amines can be readily determined as to whether in combination with a given carboxylic acid the tertiary amine is an effective tertiary amine through routine experimentation, as by forming the salt, combining the salt with polyurethane precursors, exposing the resulting composition to heat and determining whether the catalyst salt becomes unblocked above a given temperature such as above about 135° C. As such, certain tertiary amines may work with a given carboxylic acid but not with other carboxylic acids. In general, the effective tertiary amines contain less than 30 carbon atoms, and are aliphatic amines which may optionally include additional functionality such as one or more ether and/or one or more alcohol groups. Representative examples of such tertiary amines include but are not limited to N,N-dimethylcyclohexylamine (which can be referred to as "DMCHA"), pentamethyldiethlenetriamine (which can be referred to as "PMDETA"), N,N-dimethyl-2 (2-aminoethyoxy)ethanol (which can be referred to as "DMDGA"), pentamehyldipropylenetriamine (currently available commercially from Huntsman under the trade name ZR-40), tetramethyldipropylenetriamine (currently available commercially from Huntsman under the trade name ZR-50B), dimethylaminoethoxyethanol, N,N,N'-trimethylaminoethyl-ethanolamine, 2-(dimethylamino)-ethanol, and combinations thereof. In one embodiment, the tertiary amine is dimethylaminoethoxyethanol, N,N,N'-trimethylaminoethyl-ethanolamine, 2-(dimethylamino)-ethanol, or a combination thereof The carboxylic acids used in the practice of this invention are selected such that the carboxylic acid selected in combination with a given tertiary amine is blocked at room temperature and becomes unblocked at elevated temperature, such as above about 110° C., or above about 125° C., or above about 135° C., or higher, and may provide for example a carbonyl absorbance at 1730-1680 cm$^{-1}$ of at least 0.5 above 135° C. These carboxylic acids may be referred to as effective carboxylic acids, in the context of this invention. As such, certain carboxylic acids may work with a given tertiary amine but not with other tertiary amines. Carboxylic acids can be readily determined as to whether in combination with a given tertiary amine the carboxylic acid is an effective carboxylic acid through routine experimentation, as by forming the salt, combining the salt with polyurethane precursors, exposing the resulting composition to heat and determining whether the catalyst salt becomes unblocked above about 110° C., or above about 125° C., or above about 135° C., or higher. In general, the effective carboxylic acids contain less than 30 carbons, and may optionally include additional functionality such as one or more ether and/or one or more alcohol groups. Representative examples of such carboxylic acids include but are not limited to oxalic acid, salicylic acid, and combinations thereof.

Polyurethane is a well known polymer which, in general, is made by reacting diisocyanate, polyol, and the catalyst. A number of different kinds of polyurethanes can be produced depending on the nature of the polyol used and degree of cross-linking achieved, for example. If the polyurethane is a foam, a suitable blowing agent should be included, such as water as is known in the art. Polyurethane foams generally have a higher amount of cross-linking. Aliphatic, cycloaliphatic, aromatic, and heterocyclic diisocyanates can be used as starting materials, which in general may contain up to about 20 carbon atoms. Representative examples of such diisocyanates include but are not limited to naphthalene bis (4-phenyl isocyanate), 4,4'-diphenylmethane diisocyanate, 1,3- and 1,4-phenylene diisocyanate, toluene 2,4- and 2,6-diisocyanate (TDI), diphenylmethane 2,4'- or 4,4'-diisocyanate (MDI), and mixtures and/or oligomers (prepolymers) thereof. If a prepolymer is employed, its molecular weight is typically about 300 to 2000. Such a prepolymer is typically made by reacting a polyol with an excess amount of diisocyanate.

The polyol can be any conventional or specialty polyol used in the polyurethane field. Typically, the polyol has two to eight hydroxyl groups. In one embodiment, the polyol has a molecular weight of from 400 to 10,000, in some instances from 600 to 5,000. The polyols can include polyesters, polyethers, polythioethers, polyacetals, polycarbonates, and polyester amides containing two to eight hydroxyl groups, and in some instances two to four hydroxyl groups.

In general, the diisocyanate and polyol are employed so as to provide a NCO/OH ratio of from 1.1:1 to 10:1, typically 1.5:1 to 5:1.

For polyurethane formed from the heat activated salt catalyst of this invention, the polyurethane is made by first combining the polyurethane precursors (diisocyanate, polyol, catalyst, and any other additives such as a blowing agent if foam is desired). Advantageously, the salt catalyst of this invention does not initiate polyurethane formation at room temperature. Next, the precursor composition is heated to unblock the salt, whereby the unblocked tertiary amine catalyst initiates polyurethane formation.

The polyurethane compositions according to the invention may be applied as one or more layers to substrates by known methods such as spraying, brush coating, immersion or flooding or by means of rollers or doctor applicators. A substrate to be coated may be treated with suitable primers before the process according to the invention is carried out. The process according to the invention is suitable for the formation of coatings on any substrates, e.g., metals, plastics, wood or glass. The polyurethane compositions may also be used to form articles per se.

The amine/carboxylic acid salt of this invention can be used as a catalyst for polyurethane in the production of structural product based on wood materials. A representative example of such a structural product is an orientated strand board (OSB), which may be described as an engineered, mat-formed panel product made of strands, flakes, or wafers sliced from wood logs that is bonded with a polyurethane binder under heat and pressure. The wood materials that can be employed in the practice of this invention may vary widely. Representative examples of such wood materials include but are not limited to wood, bark, cork, bagasse, straw, flax, bamboo, alfa grass, rice husks, sisal, and coconut fibers. The material may be present in the form of granules, chips, fibers, or flour. The materials may have an intrinsic water content of 0 to 35 percent by weight, frequently from 5 to 25 percent by weight. The wood material is typically mixed with the polyurethane precursors (i.e., the diisocyanate, polyol, and catalyst) so as to provide a final composition that contains from about 1 to about 50, more typically 1 to 15 percent by weight, of the polyurethane precursors. Typically, the wood material is sprayed with these materials to effect mixing, as is known to one of skill in the art. An advantage of this invention is that the catalyst has essentially no catalytic effect until heat activated above an elevated temperature such as above about 110° C., above about 125° C., or above about 135° C. The polyurethane so formed serves as a binder for the wood material to hold the compress molded product together.

When sprayed, the catalyst may be sprayed in admixture with water or one or more organic solvents. For example, ethylene carbonate, propylene carbonate, or mixtures thereof can be employed as a solvent so that application of the catalyst. In general, an organic solvent should not react with the diisocyanate or polyol, evaporate readily, and be compliant with environmental regulations for a given end use. Additional representative classes of organic solvents that can be employed include but are not limited to aprotic organic solvents capable of solubilizing the components, such as esters including ethyl acetate, propyl acetate, and butyl acetate, ethers, hydrocarbons, ketones, amides, and so on. Additional examples of suitable solvents include xylene, methyl isobutyl ketone, methoxypropyl acetate, N-methyl pyrrolidone, Solvesso solvent, petroleum hydrocarbons, isobutanol, butyl glycol, chlorobenzenes and mixtures of such solvents.

The mixture of wood product and polymeric precursors are then typically compacted in a mold. Next the compacted mixture is exposed to rapid heating so that at least a portion of the compacted mixture achieves a temperature above about 135° C., for example, often under pressure up to 3 atmospheres, though atmospheric and reduced pressure may also be used. The temperature of the heat applied to the compacted material to be treated is typically up to 180° C. to 200° C., though higher and lower temperatures can be used. Typically a temperature gradient develops over the molded product, with temperatures above 135° C. in at least a portion of the product, thereby initiating unblocking of the salt and thus initiating curing of the polyurethane.

Other materials useful in the reaction may include surfactants, polyols, water, wood products, plastasizers, mold release agents, and flame retardants, as well as other common polyurethane additives.

For example, an ultraviolet stabilizer can be employed in the practice of this invention. Such ultraviolet stabilizers may include a sterically hindered piperidine derivative, such as an alkyl substituted hydroxy piperidine derivative. In one embodiment, the ultraviolet stabilizer includes the reaction product of an ester of a carboxylic acid and to alkyl substituted hydroxy piperidines. In one embodiment, the ultraviolet stabilizer is bis-(1, 2, 2, 6, 6-tetramethyl-4-piperidinyl) sebacate, known as TINUVIN™ 765 and commercially available from Ciba-Geigy.

An UV absorber can be used in the instant invention, and may generally include a substituted benzotriazole, such as a phenyl substituted benzotriazole. In one embodiment, the UV stabilizer is a hydroxyl, alkyl substituted benzotriazole. In another embodiment, the UV stabilizer is 2-(2'-hydroxy-3',5'-di-tert-amylphenyl)benzotriazole, known as TINUVIN™ and commercially available from Ciba-Geigy.

An antioxidant may be used in the instant invention such as a substituted, sterically hindered phenol, such as a substituted ester of hydroxyhydrocinnamic acid. In one embodiment, the antioxidant element is a 3,5-dialkyl ester of hydroxyhydrocinnamic acid, and another embodiment is octadecyl 3,5-di-tert-butyl-4-hydroxyhydrocinnamate, known as IRGANOX™ 1076 and commercially available from Ciba-Geigy.

The amount of additive incorporated in the polyurethane depends on several factors, including the desired stability of the polyurethane, so the amount of additive can be adjusted according to the intended use of the polyurethane. Generally, a useful amount of additive in the polyurethane can be an amount of up to about 5 percent by weight, and in one embodiment is in an amount of from about 0.5 to about 3 percent by weight.

The following examples are illustrative of this invention and are not intended to limit the scope of the invention or claims hereto. Unless otherwise denoted all percentages are by weight. Example 1 describes the synthesis of various acid blocked amine catalysts. Example 2 illustrates the effectiveness of these derivatives over the control material. The control material, catalyst G, is the material described in U.S. Pat. No. 6,007,649.

EXAMPLE 1

Preparation of Catalysts

The general procedures for these three examples are as follows. To a reactor containing a stirrer bar, carboxylic acid and water (which is optional in the practice of this invention) were added then stirred for 10 minutes. The tertiary amine was then added slowly over a thirty-minute period with stirring. The mixture was then stirred for an additional 10 minutes.

| Catalyst | Acid | Amine | Mole ratio amine/acid | Water, wt % |
|---|---|---|---|---|
| A | Oxalic | JEFFCAT ZR-70 | 1.0 | 20 |
| B (comparison) | Oxalic | JEFFCAT ZR-70 | 2.0 | 20 |
| C | Oxalic | JEFFCAT DMEA | 1.0 | 20 |
| D | Oxalic | JEFFCAT Z-110 | 1.0 | 20 |
| F (comparison) | Malonic | JEFFCAT ZR-70 | 2.0 | 20 |
| G (comparison) | Malonic | JEFFCAT DMEA | 1.0 | 20 |
| H | Salicylic | JEFFCAT ZR-70 | 1.0 | 0 |
| I | Salicylic | JEFFCAT DMEA | 1.0 | 20 |
| J | Salicylic | JEFFCAT Z-110 | 1.0 | 20 |
| K (comparison) | Adipic | JEFFCAT ZR-70 | 1.0 | 20 |
| L (comparison) | Adipic | JEFFCAT Z-110 | 1.0 | 20 |
| M (comparison) | Succinic | JEFFCAT ZR-70 | 0.63 | 20 |
| N (comparison) | Maleic | JEFFCAT ZR-70 | 1.0 | 27 |
| O (comparison) | Oxalic | JEFFCAT DPA | 1.0 | 20 |
| P (comparison) | Lactic | JEFFCAT ZR-70 | 1.0 | 7 |
| Q (comparison) | Oxalic | JEFFCAT ZF-20 | 1.0 | 20 |
| R (comparison) | Formic | JEFFCAT ZR-70 | 1.0 | 1 |

JEFFCAT ZR-70: dimethylaminoethoxyethanol (which may also be referred to as N,N-dimethyl-2-(2-aminoethoxy)ethanol)
JEFFCAT Z-110: N,N,N'-trimethylaminoethyl-ethanolamine
JEFFCAT DMEA: ethanol, 2-(dimethylamino)- (which may also be referred to as dimethylethanolamine)
JEFFCAT ZF-20: 2,2'-oxybis(N,N-dimethylethanamine)
JEFFCAT DPA: 2-propanol, 1,1'-((3-(dimethylamino)propyl)imino)bis

EXAMPLE 2

FTIR Analysis of the Reaction of the Catalyst and an Isocyanate Component

The effect that these catalysts have on a PIR foam was determined by using a REACTFTIR 1000 instrument using a heated probe. The heated probe was programmed to start at 70 C and hold at this temperature for 10 minutes. It was ramped up to 180 C over a thirty-minute period. At this point, it was held for 15 minutes at 180 C. Approximately 574 FTIR spectra were recorded during this time period from 800-4000 $cm^{-1}$. The formulation used to test these catalyst consisted of a pre-blend of RUBINATE 1840 (70 pbw), diisononylphthalate (20 pbw), and Tegostab B-8407, (7.0 pbw). Prior to placing several drops unto the FTIR probe, 0.6 pbw of water and an appropriate amount of acid blocked catalyst, 1.73 mmole, was mixed into the pre-blend. The amounts used are shown in the following Table.

| Catalyst | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| A | 0.46 | | | | | | | | | | | | | | | |
| B | | 0.37 | | | | | | | | | | | | | | |
| C | | | 0.39 | | | | | | | | | | | | | |
| D | | | | 0.49 | | | | | | | | | | | | |
| F | | | | | 0.51 | | | | | | | | | | | |
| G | | | | | | 0.42 | | | | | | | | | | |

-continued

| Catalyst | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| H | | | | | | | 0.47 | | | | | | | | | |
| J | | | | | | | | 0.62 | | | | | | | | |
| K | | | | | | | | | 0.60 | | | | | | | |
| L | | | | | | | | | | 0.64 | | | | | | |
| M | | | | | | | | | | | 0.52 | | | | | |
| N | | | | | | | | | | | | 0.52 | | | | |
| P | | | | | | | | | | | | | 0.41 | | | |
| Q | | | | | | | | | | | | | | 0.51 | | |
| R | | | | | | | | | | | | | | | 031 | |
| S (JEFFCAT ZR-70) | | | | | | | | | | | | | | | | 0.23 |

The FIGS. show the effect that the catalysts have on either the isocyanate or carbonyl absorbance. Isocyanate absorbance will decrease over time as the isocyanate is consumed. Carbonyl absorbance will increase as the amount of carbonyl absorbing species increases in the reacting mixture. The graph of the temperature profile is also shown in all of these graphs. The right side of each graph shows the temperature scale. Inspection of some of the these graphs will show that, at a certain temperature, either a sharp decrease in isocyanate absorbance, which translates to using up the isocyanate quicker, or a sharp rise in carbonyl absorbance, which translates to forming more carbonyl species. These carbonyl species are either from the reaction of the isocyanate and water, isocyanate and polyol, or trimerization of the isocyanate into an isocyanurate material or any combination of these reactions.

FIGS. 1 and 2 shows the difference in isocyanate and carbonyl absorbance between a catalyzed (JEFFCAT ZR-70) or unblocked system and a non-catalyzed system. The catalyzed system reacts quicker than the uncatalyzed system. The catalyzed system is not blocked in any manner. For an ideal blocked catalyst, the isocyanate absorbance should closely follow the uncatalyzed system but should accelerate at some point and start consuming isocyanate.

The following figures illustrate the improvement over the art, which uses JEFFCAT DMEA and malonic acid (catalyst G). A delay is shown for this derivative but it never kicks in to accelerate the consumption of the isocyanate, FIG. 3. It does slowly use up the isocyanate at a greater rate than the uncatalyzed system. It functions as a blocked catalyst but does not unblock at any particular temperature. There is a point where formation of the carbonyl species slowly increases, as shown in FIG. 4.

An improvement is shown in FIGS. 3 and 4 by the delay of JEFFCAT DMEA and oxalic acid (catalyst C) and in particular at about 170° C. where this derivative starts to accelerate the consumption of the isocyanate and the formation of carbonyl species. The higher carbonyl absorbance of the JEFFCAT DMEA and oxalic acid shows that a higher concentration of the carbonyl species is formed from this catalyst.

A further improvement of this invention is illustrated by the catalyst composed of JEFFCAT ZR-70 and oxalic acid (catalyst A). Again, as with JEFFCAT DMEA and oxalic acid, there is a point at about 150° C. in the isocyanate absorbance where JEFFCAT ZR-70 and oxalic acid accelerates the consumption of the isocyanate. This trend is also seen in the carbonyl absorbance. Surprisingly, the temperature of the conversion of the isocyanate and formation of carbonyl species occurs at a lower temperature for JEFFCAT ZR-70 than JEFFCAT DMEA, that is, 150° C. versus 170° C.

The uniqueness of the salt of JEFFCAT ZR-70 and oxalic acid is further illustrated by observing the isocyanate and carbonyl absorbencies profiles of JEFFCAT ZR-70 and malonic acid (catalyst F) and compare it with the unblocked JEFFCAT ZR-70. They are practically identical. There is no delay for catalyst F like there is with catalyst A.

Another surprising aspect of this invention is that JEFFCAT Z-110 also shows the unusual effect of blocking and then unblocking when a certain temperature is reached. This is shown in FIGS. 5 and 6. The temperature at which the JEFFCAT Z-110+oxalic acid (catalyst D) becomes unblocked and starts to consume isocyanate at a faster rate is lower than the salt of JEFFCAT ZR-70 and oxalic acid (catalyst A).

Another acid that was found to work with these amine catalysts to block and then unblock at elevated temperatures is salicylic acid. Salts of JEFFCAT ZR-70 (catalyst H) and JEFFCAT Z-110 (catalyst J) are also shown in these figures. Close inspection of the first 500 seconds with the salicylic acid derivative shows a quick isocyanate consumption followed by a somewhat flat consumption of the isocyanate up until the catalyst becomes active or unblocks similar trend is seen in the isocyanurate absorbance.

The reaction of JEFFCAT ZR-70/oxalic acid was done in a 1/1 mole ratio (catalyst A) and a 2/1 mole ratio (catalyst B). The 2/1 mole ratio was not as effective at blocking or delaying the isocyanate consumption or isocyanurate formation as the 1/1 salt, as seen FIGS. 7 and 8. The 2/1 mole ratio salt did not show any acceleration in isocyanate consumption as opposed to the 1/1 mole ratio salt, which did.

Other catalysts which did not show any signs of blocking and unblocking, and thus are comparative examples, are shown in FIGS. 9-12. These examples further demonstrate the uniqueness of the catalysts of this invention.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A tertiary amine-carboxylic acid salt that is blocked at room temperature and becomes unblocked at an elevated temperature, wherein the tertiary amine is N,N-dimethyl-2-(2-aminoethoxy)ethanol and the carboxylic acid is oxalic acid.

2. The acid salt of claim 1, wherein the tertiary amine further comprises N,N-dimethylcyclohexylamine, pentamethyldiethlenetriamine, pentamethyldipropylentriamine, tetramethyldipropylenetriamine, dimethylaminoethoxyethanol, N,N,N'-trimethylaminoethyl-ethanolamine, 2-(dimethylamino)-ethanol, or a combination thereof.

3. The acid salt of claim 1, wherein the tertiary amine further comprises dimethylaminoethoxyethanol, N,N,N'-trimethylaminoethyl-ethanolamine, 2-(dimethylamino)-ethanol, or a combination thereof.

4. The acid salt of claim 1, wherein the carboxylic acid further comprises a second carboxylic acid that contains less than 30 carbons.

5. The acid salt of claim 1, wherein the carboxylic acid further comprises salicylic acid.

6. The acid salt of claim 1, wherein the tertiary amine and the carboxylic acid are present in a mole ratio of about 1:1.

7. The acid salt of claim 1, wherein the mole ratio of tertiary amine to carboxylic acid is less than about 1.5.

8. The acid salt of claim 1, wherein the mole ratio of tertiary amine to carboxylic acid from about 0.9:1 to about 1.1.

9. The acid salt of claim 1, wherein the acid salt produces a carbonyl absorbance of at 1730-1680 $cm^{-1}$ of at least 0.5 above 135° C.

10. The acid salt of claim 1, wherein the mole ratio of tertiary amine to carboxylic acid is less than 2:1.

* * * * *